United States Patent
Montanari et al.

(10) Patent No.: US 9,744,019 B2
(45) Date of Patent: Aug. 29, 2017

(54) FABRIC WITH BARBS COATED WITH A WATER-SOLUBLE MATERIAL

(75) Inventors: Suzelei Montanari, Trevoux (FR);
Pearl Rey, Saint Nicolas de Macherin (FR)

(73) Assignee: SOFRADIM PRODUCTION, Trevoux (FR)

( * ) Notice: Subject to any disclaimer, the term of this patent is extended or adjusted under 35 U.S.C. 154(b) by 102 days.

(21) Appl. No.: 13/393,867

(22) PCT Filed: Sep. 6, 2010

(86) PCT No.: PCT/FR2010/051843
§ 371 (c)(1),
(2), (4) Date: Mar. 2, 2012

(87) PCT Pub. No.: WO2011/027087
PCT Pub. Date: Mar. 10, 2011

(65) Prior Publication Data
US 2012/0165937 A1 Jun. 28, 2012

(30) Foreign Application Priority Data
Sep. 4, 2009 (FR) .................................. 09 56038

(51) Int. Cl.
*A61F 2/02* (2006.01)
*A61B 17/03* (2006.01)
(Continued)

(52) U.S. Cl.
CPC ............ *A61F 2/0063* (2013.01); *A61L 31/10* (2013.01); *A61L 31/14* (2013.01); *D04B 21/12* (2013.01); *A61F 2/0077* (2013.01); *A61F 2002/30322* (2013.01); *A61F 2220/0016* (2013.01); *A61F 2250/0026* (2013.01);
(Continued)

(58) Field of Classification Search
CPC .................................. A61F 2/02; A61B 17/03
USPC ........ 623/11.11, 23.72–23.76; 606/151–156, 606/213–215; 128/899; 427/2.24
See application file for complete search history.

(56) References Cited

U.S. PATENT DOCUMENTS 5,079,034 A * 1/1992 Miyake et al. ............... 427/521
5,739,176 A * 4/1998 Dunn et al. ................... 523/113
(Continued)

FOREIGN PATENT DOCUMENTS

FR 2 924 330 A1 6/2009
WO 01/81667 A1 11/2001
(Continued)

OTHER PUBLICATIONS

International Search Report for Application No. PCT/FR2010/051843 mailed Dec. 15, 2010.
(Continued)

*Primary Examiner* — Yashita Sharma

(57) ABSTRACT

The present invention relates to a prosthetic fabric comprising an arrangement of yarns defining at least two faces for said fabric, said fabric comprising, on at least one of its faces, one or more barbs that protrude outwards relative to said face, characterized in that said barbs are covered with a coating made of a water-soluble biocompatible material. The invention also relates to a process for obtaining such a fabric and to prostheses obtained from such a fabric.

21 Claims, 1 Drawing Sheet

(51) Int. Cl.
*A61F 2/00* (2006.01)
*A61L 31/10* (2006.01)
*A61L 31/14* (2006.01)
*D04B 21/12* (2006.01)
*A61F 2/30* (2006.01)

(52) U.S. Cl.
CPC ................. *A61F 2250/0031* (2013.01); *D10B 2501/0632* (2013.01); *D10B 2509/08* (2013.01)

(56) References Cited

U.S. PATENT DOCUMENTS

| | | |
|---|---|---|
| 6,596,002 B2* | 7/2003 | Therin et al. .................. 606/151 |
| 2002/0052612 A1* | 5/2002 | Schmitt et al. ................ 606/151 |
| 2005/0079201 A1* | 4/2005 | Rathenow et al. ............ 424/424 |
| 2007/0100432 A1* | 5/2007 | Case et al. .................... 623/1.15 |
| 2008/0107706 A1* | 5/2008 | Lopez ........................... 424/423 |
| 2009/0192532 A1* | 7/2009 | Spinnler et al. ............... 606/153 |
| 2010/0180912 A1* | 7/2010 | Ochs .................... A61C 15/042 132/329 |

FOREIGN PATENT DOCUMENTS

| | | |
|---|---|---|
| WO | 0180773 A1 | 11/2001 |
| WO | 2009/039429 A1 | 3/2009 |

OTHER PUBLICATIONS

English translation of corresponding Japanese Office Action, Application No. JP 2012-527373 mailed Sep. 2, 2014.

* cited by examiner

FABRIC WITH BARBS COATED WITH A WATER-SOLUBLE MATERIAL

CROSS-REFERENCE TO RELATED APPLICATIONS

This application is a U.S. National Stage Application filed under 35 U.S.C. §371(a) of International Application No. PCT/FR2010/051843, filed Sep. 6, 2010, which claims the benefit of and priority to French Application 09/56038 filed Sep. 4, 2009, the entire contents of which are incorporated by reference herein.

The present invention relates to a prosthetic fabric equipped with barbs covered with a water-soluble coating. Such a fabric can particularly be used for producing wall-reinforcing prostheses intended to be introduced into a patient by coelioscopy.

Wall-reinforcing prostheses, for example prostheses for reinforcing the abdominal wall, are widely used in the surgical field. These prostheses are intended for treating hernias by temporarily or permanently filling a tissue defect. These prostheses are generally made from a biocompatible prosthetic fabric and may have several shapes, rectangular, round, oval, depending on the anatomical structure to which they must be fitted. Some of these prostheses are made from entirely bioresorbable yarns and are intended to disappear after having carried out their reinforcing role until cell colonization takes place and tissue rehabilitation takes over. Other prostheses comprise non-bioresorbable yarns and are intended to remain permanently in the body of the patient.

Some of these prostheses are made from a knit, weaving or else non-woven arrangement of yarns, comprising barbed naps that protrude outwards from one face of the prosthesis: these barbs constitute hooks capable of being fastened either to another prosthetic fabric, belonging to the same prosthesis or not, or directly to the biological tissues, such as for example the abdominal wall. Certain prostheses may also comprise barbs on each of their two faces.

Furthermore, for the sake of minimizing the traumatisms subsequent to any surgical operation, patients are increasingly often operated on via coelioscopic surgery when the type of operation carried out permits it. Coelioscopic surgery requires only very small incisions, through which a trocar is passed, within which the prosthesis is conveyed to the implantation site. Thus open surgery is avoided and the patient can leave hospital rapidly. Coelioscopic surgery is particularly popular in surgical operations carried out in the abdomen, such as for example the treatment of hernias.

However, the trocars used in coelioscopic surgery generally have a relatively small calibrated diameter, which may vary, for example, from 5 to 15 mm, in order to reduce the size of the incision made as much as possible. The prosthesis must therefore be conveyed within a channel of reduced diameter and it must then be deployed to the implantation site.

In order to carry out this step, the prosthesis is generally wound around on itself in order to make it slide in the channel of the trocar. However, when the prosthetic fabric forming the prosthesis comprises barbs on one face, it may happen that these barbs, due to the fact that they are not protected, become entangled in the fabric or are damaged during the winding of the prosthesis or when it is conveyed through the trocar to the implantation site.

Thus, there remains the need for a prosthetic fabric comprising barbed naps, that can be used for manufacturing prostheses, such as for example abdominal wall reinforcements, capable of being conveyed within a channel such as that of a trocar, without damaging the barbs, and capable of being completely deployed once it has reached the implantation site in the body of the patient.

The present invention aims to remedy such a need.

A first aspect of the present invention relates to a prosthetic fabric comprising an arrangement of yarns defining at least two faces for said fabric, said fabric comprising on at least one of its faces, one or more barbs that protrude outwards relative to said face, characterized in that said barbs are covered with a coating made of a water-soluble biocompatible material.

The expression "water-soluble material" is understood, within the meaning of the present application, to mean a material capable of dissolving in an aqueous composition such as water or biological fluids, for example at ambient temperature, either approximately at a temperature of around 20 to 25° C., or at any higher temperature and in particular at the temperature of the human body, in other words at a temperature of around 37° C.

Preferably, the water-soluble material of the fabric according to the invention is in set or solid form at a temperature less than or equal to 35° C., when it is not in contact with an aqueous composition.

Thus, when the fabric according to the invention is brought into contact with water or biological fluids, in particular at the temperature of the human body, i.e. around 37° C. at the implantation site, the material covering the barbs solubilizes little by little and thus detaches from the barbs. The time necessary for the solubilization of all of the material covering the barbs makes it possible to deploy the prosthesis easily, as will be explained in greater detail below. Once the barbs are no longer covered, they can again play their role of fastening, either to another prosthetic fabric, or within a biological tissue, such as for example the abdominal wall.

In general, the material that covers the barbs, due to its water-soluble nature, has a smooth surface at a temperature of less than or equal to 25° C.: thus, when a barb covered with water-soluble material comes into contact with another barb covered with water-soluble material, they slide over one another and do not put up any resistance. Therefore, when the prosthesis is wound around on itself in order to make it slide into a trocar, the barbs become entangled with one another, but not permanently: the barbs do not hook onto one another, they slide over one another and they are easily separated from one another as soon as the prosthesis is released from the walls of the trocar in the implantation site: the prosthesis is then easily deployed before all of the water-soluble material covering the barbs is completely dissolved.

Furthermore, this necessary solubilization time, of the order of a few seconds to a few minutes, also allows the surgeon to position the prosthesis, moving it if necessary, and this being easy since, as the water-soluble material is not yet completely dissolved, the barbs slide with respect to the surrounding tissues and do not yet fasten the prosthesis as they will do once they are completely free of the coating made of water-soluble material.

In one embodiment of the invention, said water-soluble material is biodegradable.

The term "biodegradable" is understood, within the meaning of the present application, to mean a material capable of being resorbed, absorbed and/or degraded by the tissues or washed from the implantation site and disappearing in vivo after a certain time, which may vary, for example, from a few hours to a few months, depending on the chemical nature of the material.

In one embodiment, said water-soluble material is chosen from polyethylene glycols (PEGs), polyvinyl acetates (PVAs), gelatin, polyglucuronic acid, hyaluronic acid, carboxymethyl cellulose, cellulose ethers, chitosans and mixtures thereof.

For example, said water-soluble material is a polyethylene glycol having a molar mass of less than or equal to 40 000 Da, preferably less than or equal to 20 000 Da. For example, said molar mass may vary from 1000 to 20 000 Da. The polyethylene glycols having such molar masses are particularly biodegradable.

In one embodiment, said water-soluble material comprises at least one polyethylene glycol having a molar mass of around 1000 Da. Such a polyethylene glycol enables an improved solubilization.

In one embodiment, said water-soluble material also comprises a polyethylene glycol having a molar mass different from 1000 Da.

The chitosans suitable for the water-soluble material of the present invention are water-soluble chitosans or chitosan derivatives, such as, for example, the partially N-acetylated chitosans described in the publication "Water-solubility of partially N-acetylated chitosans as a function of pH: effect of chemical composition and depolymerisation", Kjell M Vårum, Mette H. Ottøy & Olav Smidsrød, Carbohydrate Polymers, 25 (1994), 65-70.

Another aspect of the present invention relates to a process for covering a prosthetic fabric comprising an arrangement of yarns defining at least two faces for said fabric, said fabric comprising on at least one of its faces, one or more barbs that protrude outwards relative to said face, characterized in that it comprises the following steps:
  a°) a composition is prepared that comprises at least one water-soluble biocompatible material in the liquid state; and
  b°) a layer of said composition is applied to said barbs.

The composition comprising the water-soluble biocompatible material in the liquid state may be in liquid, viscous or else pasty form. For example, the composition has a consistency that enables it to be spread over the barbs, for example using a brush or else a roll, or that enables the barbs to be immersed within it. In one embodiment of the process according to the invention, step b°) is carried out using a roll. Thus, the composition is uniformly spread over the roll then onto the barbs over which the roll is applied.

In one embodiment of the process according to the invention, said composition is obtained by solubilization of said water-soluble material in water, optionally by heating said composition to the melting point of said water-soluble material.

In one such embodiment, once the layer of composition is applied to the barbs, the composition is left to dry, and optionally cool, until the layer of water-soluble material coating the barbs is in the set state, that is to say solid state.

In another embodiment of the process according to the invention, said composition is obtained by heating said water-soluble material alone, to a temperature above the melting point of said water-soluble material. In such an embodiment, once the layer of composition is applied to the barbs, the composition is left to cool until the layer of water-soluble material coating the barbs is in the set state, that is to say solid state.

Another aspect of the present invention relates to a prosthesis for the treatment of hernias, manufactured from a fabric as described above or from a fabric obtained by the process described above.

The present invention will now be described in greater detail with the aid of the following description and appended figures in which.

Figure 1:
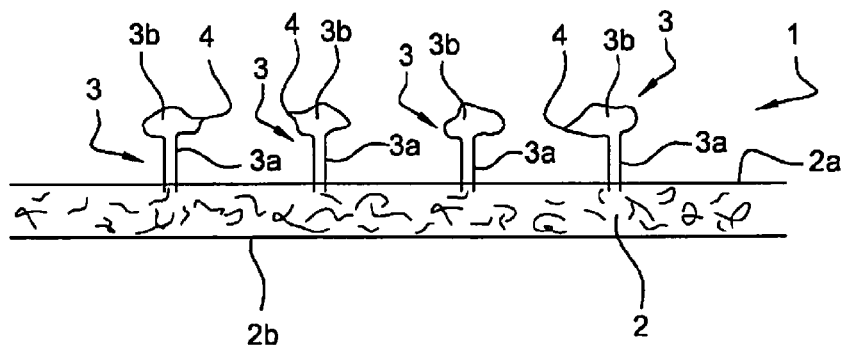
FIG. 1 is a schematic cross-sectional view of a prosthetic fabric with barbs from the prior art.

According to the present application, the expression "prosthetic fabric" is understood to mean any fabric obtained by an arrangement or an assembly of biocompatible yarns, fibres, filaments and/or multifilaments, such as a knitting, weaving, braiding or non-woven arrangement or assembly. The arrangement of yarns of the fabric according to the invention defines at least two opposite faces. The prosthetic fabric according to the invention also comprises barbs that protrude from at least one of these two faces. These barbs may protrude from said face substantially perpendicular to the plane of said face or alternatively along one or more planes inclined relative to the plane of said face. These barbs are intended to function as fastening means, either by becoming entangled in one or more arrangements of yarns, fibres, filaments and/or multifilaments of another prosthetic fabric, or by anchoring to the biological tissues, such as for example an abdominal wall.

The barbs of the prosthetic fabric according to the invention may be formed from yarns, for example, hot-melt monofilament yarns directly resulting from the arrangement of yarns forming the fabric. Such fabrics and barbs and also their manufacturing process are, for example, described in applications WO 01/81667, DE 198 32 634 or else in U.S. Pat. No. 6,596,002, U.S. Pat. No. 5,254,133.

In such cases, for example, the barbs are formed from monofilament yarns made of polylactic acid.

Alternatively, the barbs of the prosthetic fabric according to the invention may be any hook produced from any biocompatible material, attached to the arrangement of yarns forming said fabric, whether these hooks were incorporated into said fabric during the manufacture (braiding, knitting, weaving, etc.) of said arrangement of yarns or were added afterwards.

The yarns, or fibres or filaments and/or multifilaments forming the arrangement of yarns of the fabric according to the invention may be produced from any biodegradable or non-biodegradable biocompatible material. Thus, the biodegradable materials suitable for the yarns of the fabric of the present invention may be chosen from polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyethers, copolymers of these compounds and mixtures thereof. The non-biodegradable materials suitable for the yarns of the fabric of the present invention may be chosen from polyethylene terephthalate (PET), polyamides, aramids, expanded polytetrafluoroethylene, polyurethane, polyvinylidene difluoride (PVDF), polybutyl esters, PEEK (polyether ether ketone), polyolefins (such as polyethylene or polypropylene), copper alloys, silver alloys, platinum, medical grades of steel such as medical grade stainless steel, and combinations thereof.

In one embodiment of the invention, the prosthetic fabric may be provided with barbs on both its faces.

The barbs of the prosthetic fabric according to the invention are covered with a water-soluble biocompatible material.

The expression "water-soluble material" is understood within the meaning of the present application, to mean a material capable of dissolving in an aqueous composition such as water or biological fluids, for example at ambient temperature, either approximately at a temperature of around 20 to 25° C., or at any higher temperature and in particular at the temperature of the human body, in other words at a temperature of around 37° C.

Preferably, the water-soluble material is in set or solid form at ambient temperature and/or at the storage temperature of the fabric according to the invention, i.e. at a temperature approximately less than or equal to approximately 35° C., when it is not in contact with an aqueous composition.

In one embodiment of the invention, said water-soluble material is biodegradable.

The term "biodegradable" is understood, within the meaning of the present application, to mean a material capable of being resorbed, absorbed and/or degraded by the tissues or washed from the implantation site and disappearing in vivo after a certain time, which may vary, for example, from a few hours to a few months, depending on the chemical nature of the material.

In one embodiment, said water-soluble material is chosen from polyethylene glycols (PEGs), polyvinyl acetates (PVAs), gelatin, polyglucuronic acid, hyaluronic acid, carboxymethyl cellulose, cellulose ethers, chitosans and mixtures thereof.

For example, said water-soluble material is a polyethylene glycol having a molar mass of less than or equal to 40 000 Da, preferably less than or equal to 20 000 Da. Said molar mass may vary from 1000 to 20 000 Da. The polyethylene glycols having such molar masses are particularly biodegradable.

In one embodiment, said water-soluble material comprises at least one polyethylene glycol having a molar mass of around 1000 Da. Such a polyethylene glycol enables an improved solubilization.

In one embodiment, said water-soluble material also comprises a polyethylene glycol having a molar mass different from 1000 Da.

In order to prepare a fabric according to the invention, a prosthetic fabric is generally provided comprising an arrangement of yarns defining at least two faces for said fabric, said fabric comprising, on at least one of its faces, one or more barbs that protrude outwards relative to said face: such fabrics may be prepared, for example, as described in WO 01/81667.

Fabrics with barbs that are suitable for the present invention are also available commercially from the company Sofradim Production under the trade name Parietex® Progrip or else Parietene® Progrip.

The composition comprising the water-soluble material may be prepared in the form of a solution in water, if necessary by heating the solution up to the melting point of the material used. Alternatively, the composition may be prepared by heating the material alone, to a temperature above or equal to the melting point of said material, so as to obtain a liquid or viscous composition.

The composition comprising the water-soluble material in the liquid state preferably has a viscosity that enables it to be taken up using a brush or a roll. The composition is then applied to the barbs, for example with a brush or a roll. For a distribution of the composition over the barbs that is as homogeneous as possible, it is preferable to use a roll. It is also possible to vary the viscosity of the material composition, either by adapting the temperature, or by adapting the concentration of material in the composition, depending on whether it is desired to obtain a material that dissolves rapidly or not in contact with water and/or biological fluids after drying.

Once the composition comprising the material is applied to the barbs, it is left to dry and/or cool. In particular, when the composition is a solution of the water-soluble material in water, the composition is left to dry so that the water evaporates and so that essentially only the water-soluble material remains on the barbs in the end. If the composition was heated during the solubilization of the water-soluble material, the composition is also left to cool. When the composition consists of the water-soluble material alone, heated to the liquid state, the composition is left to cool to a temperature below the melting point of said material. During the drying and/or cooling as described above, the composition of water-soluble material spread over the barbs sets and coats the head of the barbs. Thus, the head of the barbs has a particularly smooth surface. When two barbs come into contact with one another, they slide over one another without putting up any resistance.

Thus, when the surgeon wishes to implant a prosthesis formed from a fabric according to the invention, he can easily wind this prosthesis around itself by folding the face provided with covered barbs towards the inside or towards the outside. Thus, the barbs are protected from rubbing against the walls of the trocar or against any other exterior element of the environment.

Once the prosthesis is conveyed to the implantation site via the trocar, the prosthesis can be unwound and deployed easily since the barbs, covered with the water-soluble material still in set form, slide over one another and do not put up any resistance. Thus, even if the barbs have become entangled during the winding of the prosthesis, it is easy to disentangle them.

The prosthesis is deployed and the barbs come, little by little, into contact with the biological fluids within which they gradually dissolve. During this gradual solubilization, which may last from a few seconds to a few minutes, the surgeon may also move the prosthesis easily in order to position it correctly with respect to the hernia defect to be filled in for example, or with respect to another prosthetic fabric present to which the surgeon wishes to attach the prosthesis.

Once all the water-soluble material present on the barbs of the fabric of the prosthesis has been dissolved in the biological fluids, optionally with the help of a saline solution that the surgeon adds in order to accelerate the solubilization of the water-soluble material, the barbs regain their coupling properties, due for example to the nature of the material forming them, and also their hook shape. The prosthesis can then be fastened, either to another fabric, or to a biological wall, the barbs not having been subjected to any damage during the transport of the prosthesis in the channel of the trocar.

The following examples illustrate the invention.

EXAMPLE 1

A prosthetic fabric, having a size of 15×10 cm$^2$ and comprising barbs as described in WO 01/81667 is provided. The barbs are produced from a monofilament yarn made of polylactic acid (PLA).

A schematic representation of a cross section of such a fabric is given in FIG. 1: the fabric 1 is formed from an arrangement 2 of yarns defining two opposite faces 2a and 2b. The fabric 1 comprises, on its face 2a, barbs 3 that protrude from this face. Each barb 3 is provided with a shaft 3a and a head 3b. As can be seen in this FIG. 1, the heads 3a of the barbs have asperities 4 that contribute to the coupling properties of the barbs.

5 g of polyethylene glycol having a molar mass of 4000 (PEG 4000 from FLUKA) the melting point of which is between 53° C. and 59° C., was heated at 60° C. in order to obtain a homogeneous liquid. The barbs of the prosthetic fabric were coated with the PEG 4000 in the liquid state using a brush or by immersing the barbs in the liquid PEG 4000 composition.

For example, if a brush is used, and as a function of the viscosity of the PEG 4000 composition, the coating may be carried out by several successive passes of brushes over the barbs.

The thus covered fabric was then left to cool at ambient temperature (at around 20° C.). The PEG 4000 composition set and coated the barbs, covering them with a smooth solid coating.

Figure 2:
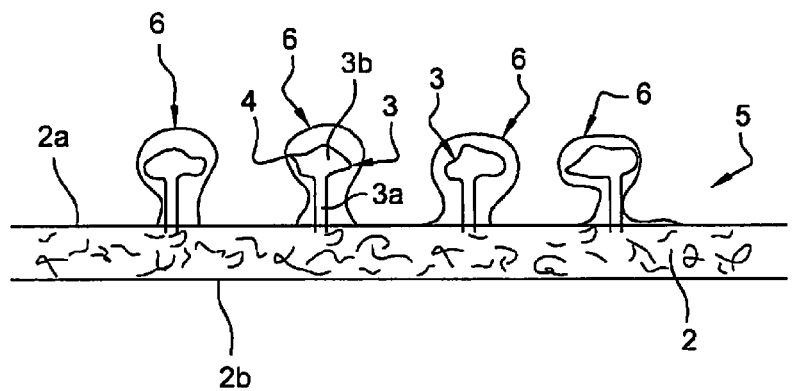
FIG. 2 is a schematic cross-sectional view of a prosthetic fabric according to the invention.

A schematic representation of a cross section of such a fabric 5 according to the invention is given in FIG. 2: the prosthetic fabric 5 according to the invention comprises barbs 3 coated with a water-soluble material, in the form of a solid layer 6 in the example represented. The solid layer 6 of water-soluble material, namely polyethylene glycol having a molecular weight of 4000 in the present example, completely coats the head 3b of each barb 3 and also a portion of the shaft 3a. As can clearly be seen in FIG. 2, the surface of the layer 6 is smooth and the heads 3b of the barbs 3 no longer have asperities 4 accessible to any other fabric.

Thus, the coating of the barbs with PEG 4000 reduces the coupling of the fabric and facilitates its handling. Under the conditions used, the mass of PEG 4000 added corresponds to around 50% of the mass of initial fabric. The fabric with the coated barbs was then washed in water at 37° C.: the barbs regain their coupling properties.

It is possible to manufacture prostheses for the treatment of hernias from fabric with barbs coated with polyethylene glycol as described in the present example, by cutting a rectangular or round shape, or a shape suitable for the anatomy of the organ to be treated, in said fabric.

The fabric with barbs coated with polyethylene glycol as described in the present example is particularly suitable for the manufacture of prostheses for the treatment of hernias via coelioscopy. Indeed, such prostheses may be wound around themselves, with the barbs on the inside and/or on the outside and may be transported thus in the channel of a trocar to the implantation site without risk of damaging the barbs. Furthermore, due to their water-soluble polyethylene glycol coating, the barbs do not obstruct the deployment firstly of the prosthesis once it has been released from the trocar at the implantation site: after a few seconds, after solubilization of the polyethylene glycol by the biological fluids, the barbs regain their coupling properties and may be used to fasten the prosthesis in the manner desired by the surgeon.

EXAMPLE 2

The same initial prosthetic fabric as in EXAMPLE 1 above and represented in FIG. 1 is provided.

Four mixtures were prepared with different proportions of polyethylene glycol having a molar mass of 4000 (PEG 4000 from FLUKA) and of polyethylene glycol having a molar mass of 1000 (PEG 1000 from FLUKA, the melting point of which is between 33° C. and 39° C.) as presented in Table 1 below. These mixtures were heated at 60° C. so as to obtain a homogeneous liquid. The barbs of samples of the prosthetic fabric were coated with said mixtures using a brush.

TABLE 1

Proportions of PEG 1000 and PEG 4000 of the various mixtures (proportions given by weight)

| Mixture | PEG 1000/ PEG 4000 proportion |
|---|---|
| No. 1 | 10/90 |
| No. 2 | 30/70 |
| No. 3 | 25/75 |
| No. 4 | 50/50 |

A prosthetic fabric 5 according to the invention as represented in FIG. 2 is obtained.

The coating of the barbs with the polyethylene glycol mixtures reduces the coupling of the fabric and facilitates its handling. Under the conditions used, the mass of mixture added varies from 30% to 100% relative to the mass of initial fabric. This data is presented in Table 2.

TABLE 2

Mass of fabric and of mixture of the various samples (referred to as Grip 1 to 9)

| Sample | Mass of fabric (mg) | Mixture | Mass of mixture (mg) | Mass of mixture (mg)/mass of fabric (mg) ratio |
|---|---|---|---|---|
| Grip 1 | 255 | No. 1 | 303 | 1.19 |
| Grip 2 | 519 | No. 1 | 388 | 0.75 |
| Grip 3 | 397 | No. 1 | 212 | 0.53 |
| Grip 4 | 713 | No. 4 | 434 | 0.61 |
| Grip 5 | 638 | No. 4 | 354 | 0.55 |
| Grip 6 | 613 | No. 3 | 468 | 0.76 |
| Grip 7 | 600 | No. 3 | 367 | 0.61 |
| Grip 8 | 627 | No. 2 | 376 | 0.60 |
| Grip 9 | 776 | No. 2 | 216 | 0.28 |

Solubilization Tests of the Mixtures:

In order to evaluate the time needed to solubilize the mixtures added to the barbs of the prosthetic fabric, the samples prepared as described above were introduced into water at 37° C. for a few seconds, until the barbs regain their coupling capabilities.

These tests showed that the mixtures solubilize rapidly (Table 3 below), and that the time needed to regain the coupling properties of the barbs is of the order of 20 seconds.

TABLE 3

Solubilization time and masses of the mixtures after the tests of solubilization in water

| Sample | Dissolution time in water at 37° C. (s) | Mass of mixture remaining after solubilization (mg) | % of mixture remaining |
|---|---|---|---|
| Grip 1 | N/A | 1 | 0.33 |
| Grip 2 | 10 | 91 | 23.45 |
| Grip 3 | 20 | 48 | 22.64 |
| Grip 4 | 10 | 73 | 16.82 |
| Grip 5 | 20 | 30 | 8.47 |
| Grip 6 | 18 | 59 | 12.85 |
| Grip 7 | 10 | 63 | 18.00 |

TABLE 3-continued

Solubilization time and masses of the mixtures after the
tests of solubilization in water

| Sample | Dissolution time in water at 37° C. (s) | Mass of mixture remaining after solubilization (mg) | % of mixture remaining |
|---|---|---|---|
| Grip 8 | 18 | 5 | 1.33 |
| Grip 9 | 10 | 32 | 16.49 |

(N/A: not applicable)

EXAMPLE 3

The same initial prosthetic fabric as in EXAMPLE 1 above, described in FIG. 1, is provided.

Seven mixtures were prepared with different proportions of polyethylene glycol having a molar mass of 4000 (PEG 4000 from FLUKA), of polyethylene glycol having a molar mass of 2000 (PEG 2000 from FLUKA) and of polyethylene glycol having a molar mass of 1000 (PEG 1000 from FLUKA) as presented in Table 4 below. These mixtures were heated at 60° C. so as to obtain a homogeneous liquid. The barbs of samples of the prosthetic fabric were coated with the mixtures using a brush.

TABLE 4

Proportions of PEG 1000, PEG 2000 and PEG 4000 of the
various mixtures (proportions given by weight)

| Mixture | PEG 1000/ PEG 2000 | PEG 1000/ PEG 4000 |
|---|---|---|
| No. 1 |  | 10/90 |
| No. 2 |  | 30/70 |
| No. 3 |  | 25/75 |
| No. 4 |  | 50/50 |
| No. 5 | 0/100 |  |
| No. 6 | 50/50 |  |
| No. 7 | 30/70 |  |

A prosthetic fabric 5 according to the invention as represented in FIG. 2 is obtained.

The coating of the barbs with the mixtures described in Table 4 reduces the coupling of the fabric and facilitates its handling. Under the conditions used, the mass of mixture added varies from 20% to 110% relative to the mass of the initial fabric. This data is presented in Table 5 below.

TABLE 5

Mass of fabric and of mixture of the various samples
(referred to as Grip 10 to 28)

| Sample | Mass of fabric (mg) | Mixture | Mass of mixture (mg) | Mixture mass (mg)/fabric mass (mg) ratio |
|---|---|---|---|---|
| Grip 10 | 650 | No. 5 | 651 | 1.00 |
| Grip 11 | 821 | No. 2 | 472 | 0.57 |
| Grip 12 | 698 | No. 4 | 242 | 0.35 |
| Grip 13 | 610 | No. 5 | 142 | 0.23 |
| Grip 14 | 490 | No. 2 | 264 | 0.54 |
| Grip 15 | 474 | No. 2 | 527 | 1.10 |
| Grip 16 | 554 | No. 5 | 427 | 0.77 |
| Grip 17 | 637 | No. 5 | 458 | 0.72 |
| Grip 18 | 609 | No. 4 | 477 | 0.78 |
| Grip 19 | 575 | No. 4 | 165 | 0.29 |
| Grip 20 | 561 | No. 6 | 314 | 0.56 |
| Grip 21 | 450 | No. 2 | 228 | 0.51 |

TABLE 5-continued

Mass of fabric and of mixture of the various samples
(referred to as Grip 10 to 28)

| Sample | Mass of fabric (mg) | Mixture | Mass of mixture (mg) | Mixture mass (mg)/fabric mass (mg) ratio |
|---|---|---|---|---|
| Grip 22 | 637 | No. 6 | 229 | 0.36 |
| Grip 23 | 526 | No. 2 | 107 | 0.20 |
| Grip 24 | 529 | No. 6 | 390 | 0.74 |
| Grip 25 | 634 | No. 7 | 434 | 0.68 |
| Grip 26 | 624 | No. 6 | 200 | 0.32 |
| Grip 27 | 598 | No. 7 | 229 | 0.38 |
| Grip 28 | 665 | No. 7 | 254 | 0.38 |

Solubilization Tests of the Mixtures:

In order to evaluate the time needed to solubilize the mixtures added to the barbs of the fabric, the samples prepared as described above were kept on wipes moistened with water at 40° C. for several predefined times (10, 15 and 20 seconds). At the end of the aforementioned times, the coupling properties of the barbs were evaluated and also the mass of residual mixture on the samples.

These tests showed that the mixture solubilizes rapidly (see Tables 6 to 8 below), and that the time needed to regain the coupling properties of the barbs is of the order of 20 seconds.

TABLE 6

Mass of the mixture after solubilization tests on wipes
moistened with water at 40° C., as a function of the
solubilization time

| Sample | Mass of mixture at 10 s (mg) | Mass of mixture at 15 s (mg) | Mass of mixture at 20 s (mg) | Mass of mixture at 30 s (mg) |
|---|---|---|---|---|
| Grip 15 | N/A | N/A | 304 | 252 |
| Grip 17 | 282 | N/A | 184 | N/A |
| Grip 18 | 396 | N/A | 335 | N/A |
| Grip 21 | 106 | N/A | 84 | N/A |
| Grip 22 | 101 | N/A | 47 | N/A |
| Grip 25 | N/A | 128 | 110 | N/A |

(N/A: not applicable)

TABLE 7

Mass of mixture (mg)/mass of fabric (mg) ratio after
solubilization tests on wipes moistened with water at
40° C., as a function of the solubilization time

| Sample | Mass of mixture (mg)/ mass of fabric (mg) ratio at 10 s | Mass of mixture (mg)/ mass of fabric (mg) ratio at 15 s | Mass of mixture (mg)/ mass of fabric (mg) ratio at 20 s | Mass of mixture (mg)/mass of fabric (mg) ratio at 30 s |
|---|---|---|---|---|
| Grip 15 | N/A | N/A | 0.64 | 0.53 |
| Grip 17 | 0.44 | N/A | 0.29 | N/A |
| Grip 18 | 0.65 | N/A | 0.55 | N/A |
| Grip 21 | 0.23 | N/A | 0.18 | N/A |
| Grip 22 | 0.16 | N/A | 0.07 | N/A |
| Grip 25 | N/A | 0.20 | 0.17 | N/A |

(N/A: not applicable)

TABLE 8

% of mixture remaining after solubilization tests on wipes
moistened with water at 40° C., as a function of the
solubilization time

| Sample | % mixture at 10 s | % mixture at 15 s | % mixture at 20 s | % mixture at 30 s |
|---|---|---|---|---|
| Grip 15 | N/A | N/A | 57.7 | 47.8 |
| Grip 17 | 61.6 | N/A | 40.2 | N/A |
| Grip 18 | 83.0 | N/A | 70.2 | N/A |
| Grip 21 | 46.5 | N/A | 36.8 | N/A |
| Grip 22 | 44.1 | N/A | 20.5 | N/A |
| Grip 25 | N/A | 29.5 | 25.3 | N/A |

(N/A: not applicable)

Tables 6 to 8 show that the amount of mixture deposited at the start plays an important role in its solubilization: for samples having a small amount of mixture, almost all the mixture deposited is found on the barbs of the fabric, which are directly in contact with the wet wipes at the time of the solubilization.

It should also be observed that the addition of PEG 1000 facilitates the solubilization. The residual amount of PEG will be lower, in a shorter period of time.

Stability of the Coating:

Given the low melting point of PEG 1000 (33° C. to 39° C.), some tests were carried out in order to evaluate the stability of the coating at 40° C. After 24 hours in an oven at 40° C., a sample coated only with PEG 1000 shows that under these conditions the PEG 1000 melts. On the other hand, the fabric coated with PEG 1000/PEG 4000 or else PEG 1000/PEG 2000 mixtures does not exhibit any modification of the coating under these same conditions.

The addition of PEG 1000 is advantageous for a rapid solubilization of the PEG mixture.

EXAMPLE 4

The same initial prosthetic fabric as in EXAMPLE 1 above and represented in FIG. 1 is provided.

Four mixtures were prepared with different proportions of polyethylene glycol having a molar mass of 2000 (PEG 2000 from FLUKA) and of polyethylene glycol having a molar mass of 1000 (PEG 1000 from FLUKA) as presented in Table 9 below. These mixtures were heated at 60° C. so as to obtain a homogeneous liquid. The barbs of samples of the fabric were coated with the mixtures using a foam roll.

TABLE 9

Proportions of PEG 1000, PEG 2000 and PEG 4000 given
as weight/weight

| Mixture | PEG 1000/ PEG 2000 |
|---|---|
| No. 5 | 0/100 |
| No. 6 | 50/50 |
| No. 7 | 30/70 |
| No. 8 | 100/0 |

Figure 3:
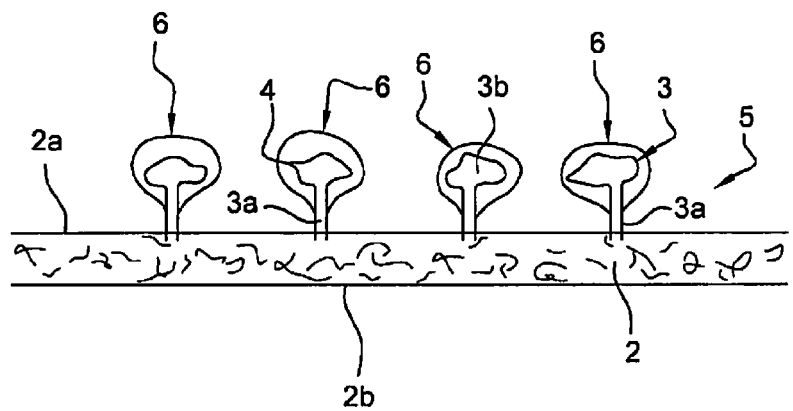
FIG. 3 is a schematic cross-sectional view of another embodiment of a fabric according to the invention.

A prosthetic fabric 5 according to the invention as represented in FIG. 3 is obtained. As can be seen in this figure, the solid layer 6 of water-soluble material, namely polyethylene glycol mixture of the present example, precisely coats the head 3b of each barb 3. The shafts 3a of the barbs remain uncoated.

Thus, the coating of the barbs with mixtures of the present example, using a roll, is highly effective. The samples thus obtained are highly homogeneous and the deposition is well directed towards the heads of the barbs of the fabric. Under the conditions used, the mass of mixture added varies from 38% to 55% relative to the mass of the initial fabric. This data is presented in Table 10 below.

Due to the coating directed towards the heads of the barbs, both an easier handling of the fabric according to the invention is obtained, as described in the preceding examples, and, at the same time, a facilitated and more rapid solubilization is obtained when the fabric is brought into contact with biological fluids.

TABLE 10

Mass of fabric and of mixture of the various samples

| Sample | Mass of fabric (mg) | Mixture | Mass of mixture (mg) | Mass of mixture (mg)/mass of fabric (mg) ratio |
|---|---|---|---|---|
| Grip 29 | 889 | No. 6 | 442 | 0.50 |
| Grip 30 | 756 | No. 6 | 415 | 0.55 |
| Grip 31 | 676 | No. 7 | 262 | 0.39 |
| Grip 32 | 634 | No. 5 | 239 | 0.38 |
| Grip 33 | 788 | No. 8 | 402 | 0.51 |

The fabrics according to the invention with barbs coated with polyethylene glycol as described in Examples 1 to 4 above are particularly suitable for the manufacture of prostheses for the treatment of hernias via coelioscopy. Indeed, such prostheses may be wound around themselves, with the barbs on the inside and/or on the outside and may be transported thus in the channel of a trocar to the implantation site without risk of damaging the barbs. Furthermore, due to their water-soluble polyethylene glycol coating, the barbs do not obstruct the deployment firstly of the prosthesis once it has been released from the trocar at the implantation site: after a few seconds the barbs regain their coupling properties and may be used to fasten the prosthesis in the manner desired by the surgeon.

What is claimed is:

1. A prosthetic fabric comprising an arrangement of yarns defining at least two faces, the fabric comprising on at least one of the faces, a plurality of barbs that protrude outward relative to the face, wherein the barbs comprise one or more filaments covered with a coating made of a water-soluble biocompatible material, wherein the water-soluble material comprises a mixture of a first polyethylene glycol having a molar mass of 1000 Da and a second polyethylene glycol having a molar mass different from 1000 Da, wherein a mass of the mixture coating the barbs ranges from 20% to 110% relative to a mass of the fabric and the barbs covered with the coating are configured to be temporarily entangled with one another while remaining easily separated by sliding over one another.

2. The fabric according to claim 1, wherein the water-soluble material is biodegradable.

3. A process for covering a prosthetic fabric comprising an arrangement of yarns defining at least two faces, the fabric comprising on at least one of the faces, a plurality barbs that protrude outward relative to the face, comprising the steps of:

preparing a composition including at least one water-soluble biocompatible material in a liquid state, wherein the water-soluble material comprises a mixture comprising a first polyethylene glycol having a molar mass of 1000 Da and a second polyethylene glycol having a molar mass different from 1000 Da; and applying a layer of the composition to the barbs to form coated barbs, wherein a mass of the composition applied to the barbs ranges from 20% to 110% relative to a mass of the fabric and the coated barbs are configured to be temporarily entangled with one another while remaining easily separated by sliding over one another.

4. The process according to claim 3, wherein the applying step is carried out using a roll.

5. The process according to claim 3, wherein the preparing step includes solubilizing the water-soluble material in water.

6. The process according to claim 3, wherein the preparing step includes heating the water-soluble material alone, to a temperature above the melting point of the water-soluble material.

7. The process according to claim 5, wherein solubilizing the water-soluble material in water includes heating the composition to a melting point of the water-soluble material.

8. A prosthesis for the treatment of hernias manufactured from a fabric obtained by the process according to claim 3.

9. The fabric according to claim 1, wherein the coating covers both a head portion and a shaft portion of the one or more barbs.

10. The fabric according to claim 1 wherein the coating covers a head portion of the one or more barbs and a shaft portion of the one or more barbs remains uncoated.

11. The fabric according to claim 1, wherein the fabric further comprises a configuration for delivery in which the fabric is wound upon itself to form an overlapped portion of the fabric and the one or more barbs are stopped from becoming entangled in the overlap portion of the fabric by the coating covering the one or more barbs.

12. A prosthetic fabric comprising an arrangement of yarns defining at least two faces, the fabric comprising on at least one of the faces, a plurality of barbs that protrude outward relative to the face, wherein the barbs comprise one or more filaments covered with a coating made of a water-soluble biocompatible material, wherein the water-soluble material comprises a mixture comprising a first polyethylene glycol having a molar mass of 1000 Da and a second polyethylene glycol having a molar mass of 2000 Da or 4000 Da, wherein a mass of the mixture coating the barbs ranges from 20% to 110% relative to a mass of the fabric and the barbs covered with the coating are configured to be temporarily entangled with one another while remaining easily separated by sliding over one another.

13. The process according claim 3, wherein the composition is applied to both a head portion and a shaft portion of the one or more barbs.

14. The process according claim 3, wherein the composition is applied to a head portion of the one or more barbs and a shaft portion of the one or more barbs remains uncoated.

15. The fabric according to claim 1, wherein the fabric comprises a configuration for delivery in which the fabric is wound around on itself and the coated barbs are temporarily entangled with one another, and the fabric further comprises a deployed configuration wherein the fabric is unwound and the coated barbs are disentangled because the coated barbs can slide over one another.

16. The fabric according to claim 1, wherein the mass of the mixture coating the barbs ranges from 30% to 100% relative to the mass of the fabric.

17. The fabric according to claim 1, wherein the mass of the mixture coating the barbs ranges from 38% to 55% relative to the mass of the fabric.

18. The fabric according to claim 1, wherein the barbs are covered with the coating individually while portions of the face between the barbs are not covered with the coating.

19. The fabric according to claim 12, wherein the mass of the mixture coating the barbs ranges from 30% to 100% relative to the mass of the fabric.

20. The fabric according to claim 12, wherein the mass of the mixture coating the barbs ranges from 38% to 55% relative to the mass of the fabric.

21. The fabric according to claim 12, wherein the barbs are covered with the coating individually while portions of the face between the barbs are not covered with the coating.

* * * * *